(12) United States Patent
Holland et al.

(10) Patent No.: US 10,688,201 B2
(45) Date of Patent: Jun. 23, 2020

(54) HEAT-INDUCED RADIOCHEMICAL LABELING OF AN IRON OXIDE NANOPARTICLE

(71) Applicant: THE GENERAL HOSPITAL CORPORATION, Boston, MA (US)

(72) Inventors: Jason Philip Holland, West Yorkshire (GB); Lee Josephson, Reading, MA (US)

(73) Assignee: The General Hospital Corporation, Boston, MA (US)

( * ) Notice: Subject to any disclaimer, the term of this patent is extended or adjusted under 35 U.S.C. 154(b) by 672 days.

(21) Appl. No.: 15/027,927

(22) PCT Filed: Oct. 9, 2014

(86) PCT No.: PCT/US2014/059891
§ 371 (c)(1),
(2) Date: Apr. 7, 2016

(87) PCT Pub. No.: WO2015/054487
PCT Pub. Date: Apr. 16, 2015

(65) Prior Publication Data
US 2016/0256581 A1 Sep. 8, 2016

Related U.S. Application Data

(60) Provisional application No. 61/889,210, filed on Oct. 10, 2013.

(51) Int. Cl.
*A61K 51/00* (2006.01)
*A61K 36/14* (2006.01)
*A61K 51/12* (2006.01)
*A61K 49/18* (2006.01)
*A61K 49/00* (2006.01)
*A61K 49/04* (2006.01)

(52) U.S. Cl.
CPC ...... *A61K 51/1244* (2013.01); *A61K 49/0002* (2013.01); *A61K 49/1818* (2013.01); *A61K 49/1863* (2013.01); *A61K 49/04* (2013.01)

(58) Field of Classification Search
None
See application file for complete search history.

(56) References Cited

U.S. PATENT DOCUMENTS

| 2004/0081617 | A1 | 4/2004 | Browitt | |
|---|---|---|---|---|
| 2012/0179029 | A1 | 7/2012 | Kircher | |
| 2013/0256583 | A1* | 10/2013 | Schlenoff | H01F 1/42 252/62.57 |

OTHER PUBLICATIONS

Castaneda et al. (J. Vis. Exp. 2011, 57, e3482).*
Bligh (Appl. Radiat. Isot. 1989, 40, 751-757).*
Nahrendorf et al. (Circulation 2008, 117, 379-387).*
Coyne (Expert Opin. Pharmacother 2009, 10, 2563-2569).*
Hudson et al. (Green Chem. 2012, 14, 622-624).*
Antoch et al., "Combined PET/MRI: A New Dimension in Whole-Body Oncology Imaging", European Journal of Nuclear Medicine and Molecular Imaging, 36 Suppl 1, 2009 (pp. 113-120).
Bengele, et al., "Biodistribution of an Ultrasmall Superparamagnetic Iron Oxide Colloid", BMS 180549, by Different Routes of Administration, Magnetic Resonance Imaging 12, 1994 (pp. 433-442).
Daldrup-Link et al., "MR Imaging of Tumor-Associated Macrophages", Oncoimmunology 1, 2012, (pp. 507-509).
Freund et al., "A Simple and Widely Applicable Method to 59Fe-Radiolabel Monodisperse Superparamagnetic Iron Oxide Nanoparticles for In Vivo Quantification Studies", ACS Nano 6, 2012 (pp. 7318-7325).
Fukuda et al., "The Role of Tumor-Associated Macrophage in Tumor Progression", Frontiers in Bioscience (Scholar edition) 4, 2012 (pp. 787-798).
Gunn et al., "Imaging Behavior of the Normal Adrenal on Ferumoxytol-Enhanced MRI: Preliminary Findings", AJR. American Journal of Roentgenology 201, 2013 (pp. 117-121).
Harisinghani et al., "Noninvasive Detection of Clinically Occult Lymph-Node Metastases in Prostate Cancer", The New England Journal of Medicine 348, 2003 (pp. 2491-2499).
Hasan et al., "Macrophage Imaging within Human Cerebral Aneurysms Wall Using Ferumoxytol-Enhanced MRI", A Pilot Study, Arteriosclerosis, Thrombosis, and Vascular Biology 32, 2012 (pp. 1032-1038).
Holland et al., "Unconventional Nuclides for Radiopharmaceuticals", Molecular Imaging 9, 2010 (pp. 1-20).
Josephson et al., "Barriers to Clinical Translation with Diagnostic Drugs. Journal of Nuclear Medicine", Official Publication, Society of Nuclear Medicine 54, 2013 (pp. 329-332).
Keliher et al., "89Zr-Labeled Dextran Nanoparticles Allow in Vivo Macrophage Imaging", Bioconjugate Chemistry 22, 2011 (pp. 2383-2389).
McCullough et al., "Ferumoxytol in Clinical Practice Implications for MRI", Journal of Magnetic Resonance Imaging : JMRI 37, 2013 (pp. 1476-1479).
Pouliquen et al., "Iron Oxide Nanoparticles for Use as an MRI Contrast Agent: Pharmacokinetics and Metabolism", Magnetic Resonance Imaging 9, 1991 (pp. 275-283).
Sauter et al., "Combined PET/MRI: One Step Further in Multimodality Imaging", Trends in Molecular Medicine 16, 2010 (pp. 508-515).
Stabi et al., "Ferumoxytol Use as an Intravenous Contrast Agent for Magnetic Resonance Angiography", The Annals of Pharmacotherapy 45, 2011 (pp. 1571-17575).

(Continued)

*Primary Examiner* — Michael G. Hartley
*Assistant Examiner* — Melissa J Perreira
(74) *Attorney, Agent, or Firm* — Nixon Peabody LLP (57) ABSTRACT

A method of synthesizing a radiolabeled nanoparticle. The method includes heating a solution including an iron oxide nanoparticle and at least one radioactive metal ion to bind the iron oxide nanoparticle and the at least one radioactive metal ion, thereby forming the radiolabeled nanoparticle. The method further includes adding a quenching agent to the solution to complex with non-bound radioactive metal ions remaining in the solution. The method further includes separating the complexed quenching agent from the radiolabeled nanoparticle.

14 Claims, 5 Drawing Sheets

(56) References Cited

OTHER PUBLICATIONS

Weissleder et al., "Superparamagnetic Iron Oxide: Pharmacokinetics and Toxicity", AJR American Journal of Roentgenology 152, 1989, (pp. 167-173).
Wong et al., "Rapid Size-Controlled Synthesis of Dextran-Coated, 64Cu-doped Iron Oxide Nanoparticles", ACS Nano 6, 2012 (pp. 3461-3467).
Zhang, H. 64Cu-DTPA-CLIO-VT680, in Molecular Imaging and Contrast Agent Database (MICAD), Bethesda MD, 2004, (1 page).
Glaus et al., "In Vivo Evaluation of 64Cu-Labeled Magnetic Nanoparticles as a Dual-Modality PET/MR Imaging Agent", Bioconjugate Chemistry, 2010, vol. 21(4) (pp. 715-722).
Hasah et al., "Macrophage Imaging Within Human Cerebral Aneurysms Wall Using Ferumoxytol-enhanced MRI: A Pilot Study", Arteriosclerosis, Thrombosis and Vascular Biology, 2012, vol. 32(4) (pp. 1032-1038).
International Search Report, PCT/US2014/59891, dated Dec. 31, 2014 (2 pages).
Written Opinion of the International Searching Authority, PCT/US2014/59891, dated Dec. 31, 2014 (5 pages).

\* cited by examiner

HEAT-INDUCED RADIOCHEMICAL LABELING OF AN IRON OXIDE NANOPARTICLE

CROSS-REFERENCE TO RELATED APPLICATIONS

This application is a U.S. National Stage of International Application No. PCT/US2014/059891, filed Oct. 9, 2014, which claims the benefit of U.S. Provisional Patent Application No. 61/889,210, filed Oct. 10, 2013, both of which are incorporated herein by reference in in their entireties.

FIELD OF THE INVENTION

The present invention relates generally to radiolabeled nanoparticles (NPs) and methods of synthesizing the same. More particularly, the present invention relates to radiolabeling an iron oxide nanoparticle (e.g., ferumoxytol) by heating it in the presence of a radioactive metal ion.

BACKGROUND

Macrophage activity is an important indicator of the normal function of the major organs of the reticuloendothelial system (e.g. liver, spleen, lymph nodes, and bone marrow). In disease, important abnormal sites of macrophage activity include tumors, inflammatory lesions, heart attack lesions, stroke lesions, and major vessel atherosclerotic plaque. Macrophage activity is often viewed by imaging uptake of nanoparticles. However, there is a lack of nanoparticles for imaging macrophage function, especially with radioactivity-based imaging modalities like positron emission tomography (PET) or single-photon emission computed tomography (SPECT).

Radiolabeled magnetic NPs can be imaged by PET or SPECT as well as by magnetic resonance imaging (MRI). The most common method of obtaining radiolabeled magnetic NPs is by the covalent attachment of chelates to the NP surface. However, labeled NPs can also be obtained by the adsorption of radiometal ions to the NP surface or by the addition of a radiometal during NP synthesis. Each method, however, has limitations. A chelator on the surface of a metal-bearing NP can be "poisoned" by small amounts of extractable metal, especially if storage of the chelate-bearing NP prior to radiolabeling is attempted. Moreover, the adsorption of metal ions to the oxide surface may not be irreversible, especially in complex biological media, and is limited to those metals that bind to the NP surface. Radiometal addition during synthesis requires the use of relatively long-lived isotopes, with purification of the radioactive NP and disposal of now radioactive liquid waste. In addition, the starting NPs used for radiolabeling typically have unknown toxicological properties and/or a lack of history of clinical use.

Figure 1:
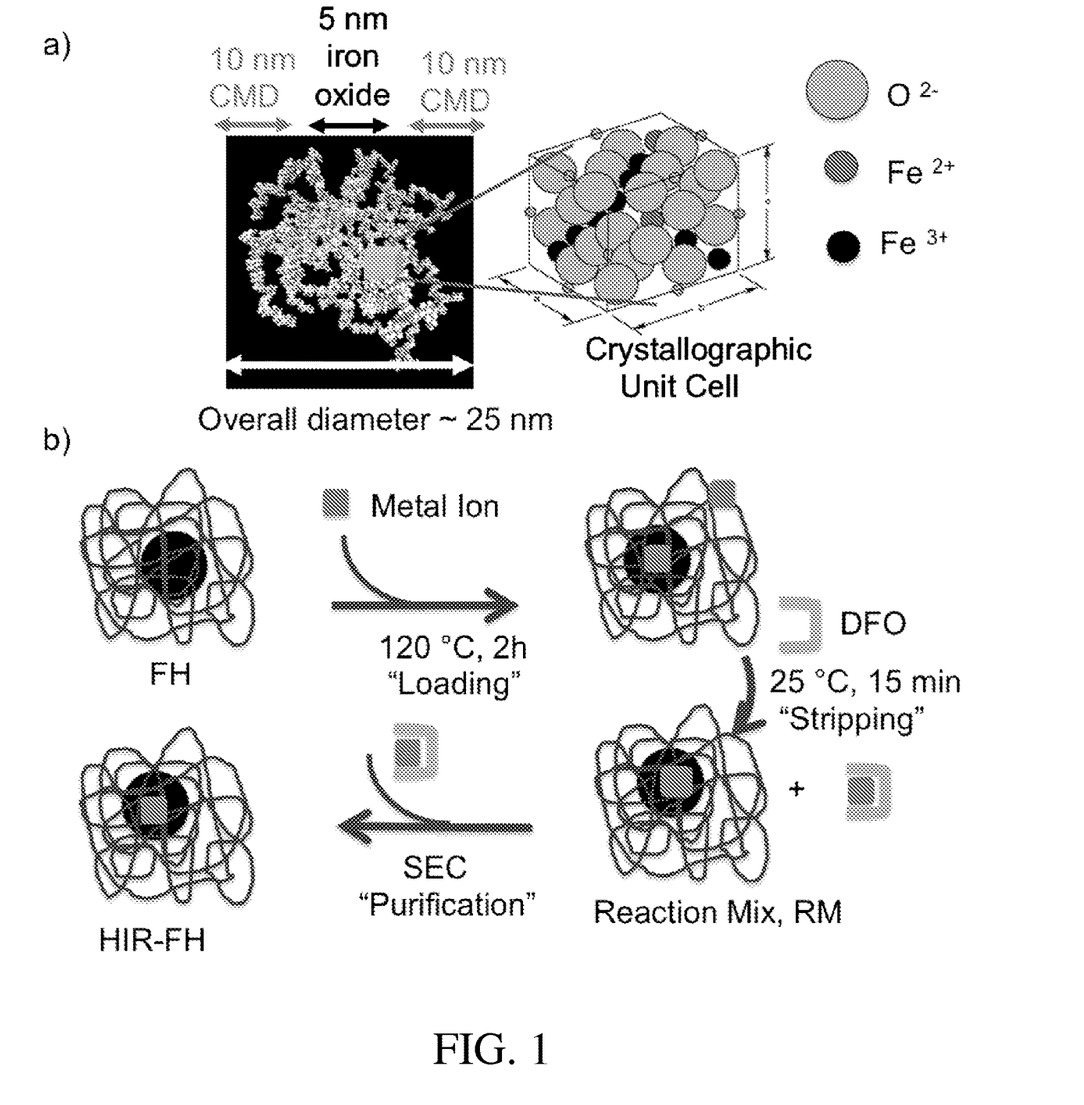
FIG. 1a illustrates the structure of FH.
FIG. 1b illustrates one process of HIR including loading, stripping, and purification of FH.

One iron oxide nanoparticle called ferumoxytol (e.g., FERAHEME® (FH), available from AMAG Pharmaceuticals, Inc., Lexington, Mass.), approved for the treatment of iron anemia, can be used to image macrophage function. The iron of ferumoxytol is superparamagnetic and alters magnetic resonance (MR) signals. The structure of FH is shown in FIG. 1a. Ferumoxytol includes a core of 5874 iron atoms present as a super-paramagnetic iron oxide and a relatively thick coating (approximately 10 nm) of carboxy-methyldextran (CMD). The overall diameter of a ferumoxytol nanoparticle is about 25 nm.

The FH NP formula is $Fe_{5874}O_{8752}$: $C_{11719}H_{18682}O_{9933}Na_{414}$. As a radiolabeling substrate, FH NP is advantageous because of its wide availability, well-understood pathways of degradation, and demonstrated clinical safety at high anemia-treating iron doses (relative to the lower iron doses that might be used in PET or SPECT imaging). FH may be used to treat iron anemia by bolus injections of roughly 500 mg of iron. FH is also used off-label to image infiltrative macrophages by MR in many clinical settings.

Although ferumoxytol is indicated for the treatment of iron anemia, the iron oxide core is superparamagnetic, and it is moderately detectable by MRI. Thus, ferumoxytol has been widely used as an MRI contrast agent for macrophages in various imaging clinical trials. Most clinical trials use ferumoxytol at or around the high dose toxicity limit, and many give poor or marginal results. Trials using ferumoxytol have been conducted in areas including neuroinflammatory states, CNS neoplasms, imaging myocardial infarction, imaging the progression of type I diabetes, imaging the metastatic status of lymph nodes, imaging central nervous system (CNS) function, and the like.

Use of ferumoxytol as an MRI agent has several limitations. First, high doses and small MR signal intensity changes are characteristic of some tissues, and the dose of ferumoxytol often cannot be increased due to iron toxicity. Some tissues have weak macrophage activity that cannot be visualized when using ferumoxytol and MRI. Moreover, MRI cannot quantify the amount of ferumoxytol in a tissue. On the other hand, PET imaging gives quantitative data on nanoparticle tissue concentrations. Moreover, FH/MRI techniques often require the administration of anemia-treating doses of 400-500 mgs of Fe to non-anemic individuals. It is estimated that heat-induced radiolabelling (HIR) FH for imaging macrophages by SPECT or PET could involve iron doses of only about 5-50 mg/person. In addition the PET imaging of radiolabeled NPs offers higher detectability of tissue NP concentrations and the ability to quantify of $^{89}Zr$ concentrations in tissues or organs. Thus, the replacement of FH/MRI with $^{89}Zr$-FH/PET or $^{111}In$/SPECT might offer advantages for imaging macrophage infiltration in various pathologies.

There are also significant barriers to developing new macrophage imaging agents. First, there are often high regulatory barriers and/or costs associated with the de novo development of clinical imaging agents. Second, current radiolabeling methods are selective for one radioactive metal or another, which limits the applications, markets, and utility of a radiolabeled nanoparticle for macrophage imaging. Third, it is desirable that the radiolabeled nanoparticle be detectable by at least two imaging modalities. This allows multimodal imaging of the same patient to enhance the quality of information obtained.

Thus, there exists a need for a simple yet general radiolabeling method for iron oxide nanoparticles that minimizes the regulatory costs associated with the clinical translation of a radiolabeled nanoparticle. It is desirable that the macrophage imaging agent meeting these conditions be detectable by at least two modalities (e.g., MR and a radioactive imaging method such as PET, SPECT, or Cerenkov imaging).

SUMMARY OF THE INVENTION

According to one embodiment, a method of synthesizing a radiolabeled nanoparticle comprises heating a solution including an iron oxide nanoparticle and at least one radioactive metal ion to bind the iron oxide nanoparticle and the at least one radioactive metal ion, thereby forming the radiolabeled nanoparticle. The method further comprises adding a quenching agent to the solution to complex with non-bound radioactive metal ions remaining in the solution. The method further comprises separating the complexed quenching agent from the radiolabeled nanoparticle.

According to another embodiment, a method of synthesizing a radiolabeled nanoparticle comprises heating a solution including a polymer-coated iron oxide nanoparticle and at least one radioactive metal ion to bind the iron oxide nanoparticle and the at least one radioactive metal ion, thereby forming the radiolabeled nanoparticle.

According to another embodiment, a radiolabeled nanoparticle comprises a polymer-coated iron oxide nanoparticle bonded to a radioactive metal ion, the bonding being configured to withstand an addition of a quenching agent.

According to another embodiment, a method of removing a radioactive metal ion from solution includes heating a solution including an iron oxide nanoparticle and at least one radioactive metal ion to bind the iron oxide nanoparticle and the at least one radioactive metal ion. The method further includes adding a quenching agent to the solution to complex with non-bound radioactive metal ions remaining in the solution. The method further includes removing the complexed quenching agent from the solution.

According to another embodiment, a method of imaging of macrophages using a heat induced radiolabeled nanoparticle includes injecting a polymer-coated iron oxide nanoparticle bonded to a radioactive metal ion into a subject such that the polymer-coated iron oxide nanoparticle bonded to a radioactive metal ion is internalized by the macrophage. The bonding between the polymer-coated iron oxide nanoparticle and the radioactive metal ion is configured to withstand an addition of a quenching agent. The method further includes using magnetic resonance imaging and radioactive imaging to detect and image the macrophage.

Additional aspects of the invention will be apparent to those of ordinary skill in the art in view of the detailed description of various embodiments, a brief description of which is provided below.

BRIEF DESCRIPTION OF THE DRAWINGS

Various advantages of the invention will become apparent upon reading the following detailed description and upon reference to the drawings.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

The embodiments described herein generally relate to radiolabeled nanoparticles and methods of synthesizing the same. More particularly, the present invention relates to radiolabeling an iron oxide nanoparticle (e.g., ferumoxytol) by heating it in the presence of a radioactive metal ion.

In the embodiments described herein, heating causes very small amounts of radioactive metal to tightly associate with an iron oxide nanoparticle so that crystal size, coating, and other properties of the iron oxide nanoparticle are not significantly affected. The association between the radioactive metal ion and the iron oxide nanoparticle is tight, as indicated by the radiolabeled nanoparticle's ability to survive the addition of a low molecular weight quenching, metal chelating agent. Because the iron oxide nanoparticle and radiolabeled iron oxide nanoparticle are physically/functionally identical (except for the resulting radioactivity of the radiolabeled nanoparticle), the considerable knowledge of the iron oxide nanoparticle's lack of toxicity and metabolism can be applied to the resulting radiolabeled nanoparticle. This benefit can, e.g., substantially decrease costs of creating diagnostic drugs developed using the embodiments of the present invention.

The radiolabeling methods of the embodiments described herein have several desirable features. For example, the radiolabeling methods use as a raw material an iron oxide nanoparticle (e.g., ferumoxytol) that is an approved drug for radiolabeling. Although ferumoxytol is used in many of the embodiments described herein, it is contemplated that other suitable iron oxide nanoparticles may also be used. Non-limiting examples of other possible iron oxides include INJECTAFERO (ferric carboxymaltose) (available from Vifor AG, Switzerland) and IMFERON® (iron dextran) (available from Benger Laboratories, England).

The methods described herein generally relate to heat induced radiolabeling of an iron oxide nanoparticle. The heating may be similar to the terminal sterilization used in manufacturing ferumoxytol. A variety of metals ions may be used to synthesize the radiolabeled iron oxide nanoparticle, such as, for example, the cations listed in Table 1 below. After heating the iron oxide nanoparticle and the radioactive metal ion, a quenching agent is added. This quenching agent both stops the nanoparticle labeling and removes any loosely-bonded metal ions on the surface of the nanoparticle. The quenching agent is then removed (e.g. by gel filtration, dialysis, spin column filtration methods, other suitable methods, or any combination thereof).

According to one method, heat is applied to a solution including ferumoxytol and a radioactive nuclide salt. A reaction between the ferumoxytol and the radioactive nuclide salt proceeds rapidly on the application of heat and mechanical agitation (such as stirring, shaking, sonication, any combination thereof, or the like). Heat may be applied until a temperature of from about 80° C. to about 150° C. is reached. In some embodiments, a temperature of from about 100° C. to about 125° C. is achieved. The pH of the solution may range from 0-14. In one embodiment, the solution is basic (i.e., the pH is greater than 7). The alkaline or slightly alkaline pH values may assist in avoiding iron dissolution. For example, the pH of the solution may range from about 7 to about 11. In some embodiments, the pH of the solution ranges from about 8 to about 9. The solution may include counter ions such as, but not limited to, halogen anions, fluoride, chloride, bromide, iodide, carboxylates, phosphates, metal salts of organic acids including metal oxalate salts, combinations thereof, or the like.

The radioactive metal ion of the radiolabeling methods described herein may have a radioactivity of about 0.01 mCi to about 50 mCi. In one embodiment, a combination of more than one radioactive metal ion or a combination of radioactive metal ion(s) and non-radioactive metal ion(s) may be used. In another embodiment, the radioactive metal ion has a radioactivity of about 0.05 mCi to about 5 mCi. The amount of the radioactive metal ion depends on factors such as the type of subject (e.g., animal/mouse or human), method of administration, therapeutic versus diagnostic intent, combinations thereof, and the like. For example, less radioactive metal ion is generally required for local administration than for intravenous (IV) administration. Also, the amount of radioactive metal ion required for therapeutic intent is generally higher than for that required for diagnostic intent.

The amount of iron in the iron oxide nanoparticle of the methods described herein may range from about 0.1 mg to about 50 mg Fe. In some embodiments, the amount of iron in the nanoparticle is from about 0.5 mg to about 5 mg Fe. The number of moles of iron (as iron oxide) may exceed the number of moles of radioactive metal ion as conditions are selected. The nanoparticles used in the embodiments described herein are generally heat stable and superparamagnetic.

Non-limiting examples of metal ions that may be employed are listed in Table 1 below. Note this table is not exhaustive and the embodiments described herein should be understood to extend to all available radioactive metal ions and chemical oxidation states of the metal ions themselves, regardless of their potential use. Alternative radionuclides of the same elements or alternative oxidation states can be employed. For example, $^{64}Cu^{2+}$ is listed in the Table 1, but the methods described herein are equally applicable to other Cu radionuclides including, e.g., $^{60}Cu$, $^{61}Cu$, $^{62}Cu$, $^{66}Cu$, and $^{67}Cu$ in either the 1+ or 2+ oxidation state. Other potential radionuclides that may be used include, but are not limited to $^{11}C$, $^{13}N$, $^{15}O$, $^{18}F$, $^{52m}Mn$, $^{68}Ga$, $^{82}Rb$, $^{110m}In$, $^{118}Sb$, $^{122}I$, $^{34m}Cl$, $^{38}K$, $^{45}Ti$, $^{51}Mn$, $^{52}Mn$, $^{52}Fe_{5874}$, $^{55}Co$, $^{64}CU$, $^{66}Ga$, $^{71}As$, $^{72}As$, $^{74}As$, $^{75}Br$, $^{76}Br$, $^{82n}Rb$, $^{86}Y$, $^{89}Zr$, $^{90}Nb$, $^{94m}Tc$, $^{120}I$, $^{124}I$, $^{67}Ga$, $^{99m}Tc$, $^{111}In$, $^{123}I$, $^{32}P$, $^{47}Sc$, $^{89}Sr$, $^{90}Y$, $^{105}Rh$, $^{111}Ag$, $^{117m}Sn$, $^{131}I$, $^{149}Pm$, $^{153}Sm$, $^{166}Ho$, $^{177}Lu$, $^{186}Re$, $^{188}Re$, $^{195m}Pt$, $^{212}Bi$, $^{213}Bi$, $^{211}At$, $^{225}Ac$, $^{230}U$, $^{82}Rb$, combinations thereof, and the like.

TABLE 1

Exemplary Metal Ions that Can Be Employed to Label NPs

| Metal ion | Emission | Half-life | Use |
|---|---|---|---|
| $^{64}Cu^{2+}$ | Positron | 12.7 h | PET |
| $^{89}Zr^{4+}$ | Positron | 78.4 | PET |
| $^{68}Ga^{3+}$ | Positron | 68 min | PET |
| $^{67}Ga^{3+}$ | Gamma | 3.26 d | SPECT |
| $^{111}In^{3+}$ | Gamma | 2.8 d | SPECT |
| $^{99m}Tc$ | Gamma | 6 h | SPECT |
| $^{223}Ra^{2+}$ | alpha | 11.4 d | therapy |
| $^{225}Ac^{3+}$ | alpha | 10.0 d | therapy |
| $^{57}Co^{2+}$ | gamma | 272 d | gamma-scintigraphy or SPECT |
| $^{177}Lu^{3+}$ | gamma | 6.6 d | therapy |
| $^{90}Y^{3+}$ | gamma | 64.0 h | therapy |

According to one embodiment, the particular metal ion used may be selected based at least in part upon the intended application.

The embodiments of the present invention do not require a change in metal oxidation state or a reducing agent. A polymer-coated, iron oxide nanoparticle/drug may be used, which may assist in reducing toxicological risks and regulatory barriers. The polymer coating assists in stabilizing the iron oxide nanoparticle from aggregation and allows the iron oxide nanoparticle to tightly bond to the radioactive metal ion. More specifically, the polymer-coated iron oxide nanoparticle may be heated to allow the radioactive metal ion to pass through the coating and tightly associate with the iron oxide nanoparticle (rather than cause the polymer coating to dissociate therefrom).

The heating step of the radiolabeling methods of the embodiments described herein may be conducted at a temperature of about 80° C. to about 150° C. for about 5 minutes to about 500 minutes. In some embodiments, the solution including the iron oxide nanoparticle and the radioactive metal ion is heated from about 60 minutes to about 150 minutes. In some embodiments, the solution is heated to a temperature of about 120° C. for about 120 minutes. Heat can be applied using any suitable method or device (e.g., using a microwave device).

After the reaction of the nanoparticle with the radioactive metal ion is complete or substantially complete, a suitable quenching agent is added to complex with any remaining unreacted or free radioactive metal ion. The quenching agent may have a low molecular weight, e.g., between about 200 and about 2000 (without any metal attached). The quenching also dissociates any loosely-bound radioactive metal ions from the iron oxide nanoparticle so that only radioactive metal tightly bound to the iron oxide nanoparticle remains bound.

It is contemplated that any suitable quenching agent or combination thereof may be used. The type of quenching agent depends, e.g., on the radioactive metal ion employed. The quenching agent may include common strong chelating agents such as, for example, desferrioxamine, desferrioxamine B (e.g., for Zr), diethylenetriamine pentaacetate (DTPA), ethylenediaminetetraacetic acid (EDTA), and macrocyclic chelates like 1,4,7,10-tetraazacyclododecane-1,4,7,10-tetraacetic acid (DOTA), 1,4,7-triazacyclononane-N,N',N"-triacetic acid (NOTA), any combinations thereof, and the like.

After quenching, the mixture may be cooled to about room temperature (e.g., about 20° C. to about 30° C.) and the quenching agent may be reduced/eliminated using any suitable techniques. For example, the mixture may be subjected to purification using, for example, size exclusion methods. Such size exclusion methods may include, but are not limited to, spin column filtration, gel column filtration (e.g., using a SEPHAROSE® G25 PD10 gel filtration device (GE Healthcare, Sweden)), or size exclusion chromatography. Chromatography may be desirable because it may also be used to demonstrate radioactivity bound to the NP and/or to indicate purity. The association of the bulk of the radioactivity with the high molecular weight fraction (corresponding with the initial nanoparticle) indicates a generally successful nanoparticle labeling reaction. After the nanoparticles have been tightly bonded the radioactive metal ion, the nanoparticles themselves remain generally functionally intact. No (or substantially no) changes to physical properties (other than the fact that the nanoparticles become radioactive) can be observed.

For therapeutic uses, the iron oxide nanoparticle may be labeled with appropriate radioactive metal ions, such as, for example, those of Table 1. To avoid dose-limiting toxicities to the liver and/or spleen that may be encountered with IV administration and/or therapeutic applications, intratumoral, peritumoral, or subcutaneous injections or local administration of the radiolabeled nanoparticle may be employed.

The ability to modify existing nanoparticle drugs like FERAHEME® with a wide range of radioactive metal ions (such as those of Table 1) has broad implications for diagnostic imaging and radiotherapy. As noted above, existing methods and clinical trials typically use ferumoxytol as an MR contrast agent. Radiolabeled ferumoxytol may be used to improve the use of ferumoxytol in diagnostic imaging for any of these applications by, e.g., using it with multimodal MRI/PET instrumentation. Radiolabeled ferumoxytol might be used as a single modality SPECT or PET agent for any of these applications, particularly when MR weak signal intensity changes are small and maximal iron doses have been reached. Radiolabeled ferumoxytol may also be used as a delivery method for administering doses of therapeutic radionuclides.

One important diagnostic use of radiolabeled nanoparticles of the embodiments described herein includes radiolabeling iron oxide nanoparticles for PET imaging of tumor-associated macrophages (TAMs), which play a key role in the maintenance, aggression, and metastases of tumors. Radiolabeled nanoparticles may be internalized by TAMs. Once a radiolabeled nanoparticle is in TAMs, it can assist in killing the tumor by killing macrophages or through radiation bystander effects on cancer cells, which occurs when radioactivity in one cell kills a second cell that is lacking radioactivity. Currently, there is no agent or imaging technology for imaging TAMs in humans. MRI of magnetic nanoparticle accumulation in TAMs is typically accomplished in animal models but requires prohibitively high doses of ferumoxytol when clinical use is considered.

Another potential use of the embodiments of the present invention is radiolabeling iron oxide nanoparticles for multimodal (PET/MRI) imaging for lymph node metastatic status. The uptake of magnetic nanoparticles by lymph nodes (after IV injection) is typically used to determine nodal metastatic status by MRI. Radiolabeled nanoparticles may be used for multimodal nodal imaging. Using the embodiments described herein, PET may indicate nodal nanoparticle concentration, and MRI may indicate the precise anatomical disposition of the PET radioactivity. MRI has been used to obtain lymph node size and intranodal features. Adding the quantitation of nodal radioactivity by PET to the high-resolution MRI of lymph nodes may improve sensitivity and specificity of lymph node MRI and/or play a major role in diagnostic imaging.

Moreover, radiolabeled iron oxide nanoparticles may add substantial value to rapid adaptation of multimodal MR/PET imager technologies.

Yet another potential use of the embodiments described herein is with image guided tumor therapy with radiolabeled iron oxide nanoparticles. A diagnostic nanoparticle such as, for example, $^{89}$Zr:ferumoxytol, may be used for image-guided therapy. In this example, $^{89}$Zr:ferumoxytol tumor uptake will be determined by PET, with nanoparticles administered by IV or locally to reduce liver and spleen uptake. A therapeutic radiolabeled ferumoxytol, such as $^{223}$Ra$^{2+}$:ferumoxytol or $^{225}$Ac$^{3+}$:ferumoxytol, may then be used for therapy.

Yet another potential use of the embodiments described herein is for removing, extracting, or immobilizing target radioactive elements in the +2, +3 or +4 oxidation state from solution through their binding to a non-radioactive iron oxide nanoparticle. An iron oxide nanoparticle may be mixed with a target radioactive metal ion, generally with a molar ratio of iron to target metal of about 50 moles of iron (or, e.g., greater than 50) to about 1 mole of target at a pH greater than about 6, and the mixture may then be heated, with stirring as needed. The stripping (chelating) agent may then be added, and low molecular weight radioactive ions bound to the stripping agent may be separated by gel filtration or ultrafiltration, filtration, centrifugation, or any other suitable separation method(s). The resulting iron oxide nanoparticle with the bound target radioactive metal can be disposed of or digested with acid to release the target metal. Non-limiting examples of ions that may be handled in this fashion are fission decay products including $^{99}$Tc, $^{126}$Sn, or $^{90}$St, or members of the actinide series.

A particular advantage of the methods described herein is that the extracted elements are incorporated into magnetic nanoparticles that can then be separated from non-magnetic particles by magnetic devices including, for example, high gradient magnetic filters.

The magnetic nanoparticles need not be non-toxic or biodegradable. Thus, they can be nanoparticles lacking a polymeric coating but ionically stabilized. Magnetic particles used for radioactive metal extraction may be ionically stabilized and composed of metals in addition to iron.

FIG. 1b illustrates one example of heat induced radiolabeling (HIR) using FH. The HIR procedure outlined in FIG. 1b consists of a loading step where small amounts of a radioactive metal ion are heated with large amounts of FH iron (e.g., about 120° C. for about 2 h), followed by a stripping step where deferoxamine (DFO) is added to remove metal ions loosely bound to the NP, followed by a purification step where size exclusion chromatography (SEC) separates the low molecular weight complexes of DFO and ions from the HIR-FH NP. For loading, the metal ion solution was first brought to a pH of about 7-8 with Na$_2$CO$_3$, then added to about 1 mg Fe as FH (about 33 µl of about 30 mg Fe/mL or about 18.9 µmoles Fe), and heated at about 120° C. for about 2 hours. For stripping, DFO (about 5 μl of about 20 mM at a pH of about 7-8 or about 0.1 μmole) was added for 15 minutes at or about room temperature. For purification, the reaction mix was added to a PD-10 column in saline. The FH fraction was concentrated with an about 10 kDa MC AMICON® centrifugal filter (EMD Millipore, Darmstadt, Germany).

HIR takes advantage of the high heat stability of the FH NP, as evidenced by the terminal (heat) sterilization step employed in its manufacture. Notably, the temperature of the HIR loading reaction may be less than that used when the drug FH is terminally sterilized during manufacture. HIR is generally considered a "chelateless" radiolabeling method because the chelate is used only after NP loading to strip away loosely bound metal ions and does not participate in the bonding of the radiometal to the NP.

The HIR procedure of FIG. 1b was used to obtain FH NPs labeled with $^{89}$Zr or $^{64}$Cu, isotopes used for PET, and with $^{111}$In, an isotope used for SPECT imaging. FIGS. 2a-f show the HIR reaction mixes with $^{89}$Zr, $^{64}$Cu, or $^{111}$In analyzed by TLC with a strong cation exchanger and water solvent in which the three DFO:metal complexes stay at the origin while the radiolabeled NP moves at the front. Although DFO is generally approved for iron removal, it has significant affinities for trivalent ions such as, for example, gallium, aluminum, and indium, and copper and binds those ions at the high DFO concentrations employed in the examples of FIGS. 2a-f. In the examples described herein, copper, indium and zirconium ions, or their DFO:metal complexes, generally remain at the origin. Radiochemical yields were greater than about 80% for $^{89}$Zr and $^{111}$In and greater than 50% for $^{64}$Cu.

A key feature of the HIR loading reaction shown in FIG. 1b is the use of a high molar ratio of NP iron to radiometal. For example, with a typical loading with $^{89}$Zr, about 1 mg of FH iron (about 17.9 μmoles Fe) was heated with about 1 mCi of $^{89}$Zr, which corresponds with a Zr mass of about 0.00025 μmoles ($^{89}$Zr specific activity of about 4000 mCi/μmoles) and gives a molar ratio of about 1 Zr to about 71,600 Fe. Thus, heat allows a small amount of $^{89}$Zr to bind to a small number of high-affinity binding sites on the FH NP. Since there are 5874 Fe atoms per FH NP, there is less than one Zr per FH NP. The stripping reaction then uses about 0.1 μmole of DFO (molar ratio of about 400 DFOs to about 1 Zr), to ensure that any Zr that remains bound to the FH NP is tightly bound. The scale used of about 1 mg Fe to obtain $^{89}$Zr-FH allowed for injections of about 4-8 mice (about 0.025 kg/mouse) at doses comparable to the FH doses used clinically, which are about 5 mg/kg. A typical FH dose for anemia treatment is about 510 mg (about 7 mg/kg).

Figures 2A, 2B:
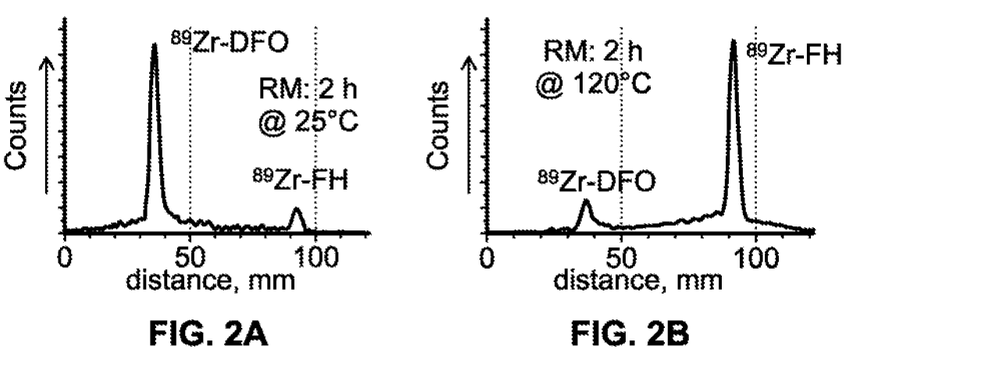
FIG. 2a illustrates the HIR of FH NPs with $^{89}$Zr, as monitored by thin layer chromatography (TLC), after about 2 h at about 25° C.
FIG. 2b illustrates the HIR of FH NPs with $^{89}$Zr, as monitored by TLC, after about 2 h at about 120° C.
Figures 2C, 2D:
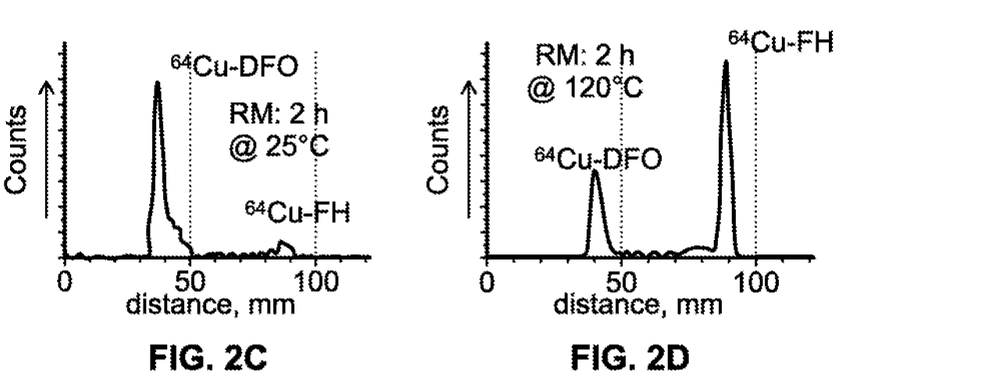
FIG. 2c illustrates the HIR of FH NPs with $^{64}$Cu, as monitored by TLC, after about 2 h at about 25° C.
FIG. 2d illustrates the HIR of FH NPs with $^{64}$Cu, as monitored by TLC, after about 2 h at about 120° C.
Figures 2E, 2F:
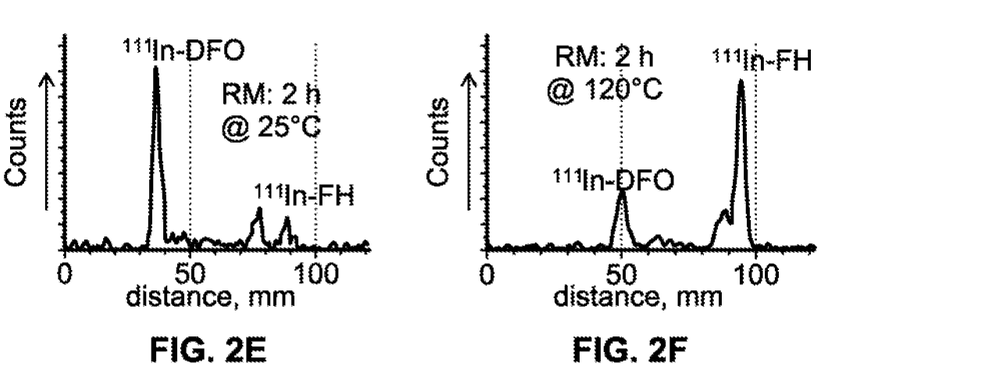
FIG. 2e illustrates the HIR of FH NPs with $^{111}$In, as monitored by TLC, after about 2 h at about 25° C.
FIG. 2f illustrates the HIR of FH NPs with $^{111}$In, as monitored by TLC, after about 2 h at about 120° C.

Before using HIR $^{89}$Zr-FH in PET imaging, its purity and stability were verified, as shown in FIGS. 2a-f. As an illustrative, non-limiting example, the procedure used to make $^{89}$Zr-FH for FIG. 2a is given. After Na$_2$CO$_3$ neutralization, the sample was split, with part heated at about 120° C. and part at about 25° C. To $^{89}$Zr (about 1.547 mCi, about 56 μl) was added water (about 44 μl) and Na$_2$CO$_3$ (about 1 M, about 56 μl) to obtain a pH of about 7-8. To one portion of $^{89}$Zr (about 52 μl, about 501 uCi) in a 5 mL Reactivial was added to water (about 200 μl) and FH (about 33.3 μl, about 1 mg Fe), and the reaction mixture was heated in an oil bath with magnetic stirring for about 2 hours. After about 2 hours, the vial was cooled down to or about room temperature in a water bath for about 15 minutes. DFO solution in chelexed water (about 5 μl, about 20 mM, pH of about 7-8) was added for an additional about 15 minutes at or about room temperature with stirring. The reaction mixture was loaded onto a PD-10 column and eluted by about 0.9% saline. The void volume product (about 454 μCi) was concentrated by centrifugation. The final about 120° C. product (about 415 μCi, about 130 μl) was >95% pure by TLC with an RCY of about 82.8%. The specific activity was about 0.023 mCi/μmol of Fe. The reaction was run using up to about 8 mCi of $^{89}$Zr, with Na$_2$CO$_3$ as needed, to achieve pH values of about 7-8 using about 1 mg Fe of FH with stripping and purification steps.

Figure 3A:
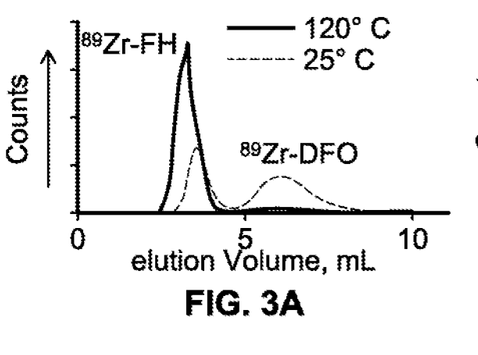
FIG. 3a illustrates an SEC chromatogram of FH incubated with $^{89}$Zr at the indicated temperatures with deferoxamine (DFO) added.
Figure 3B:
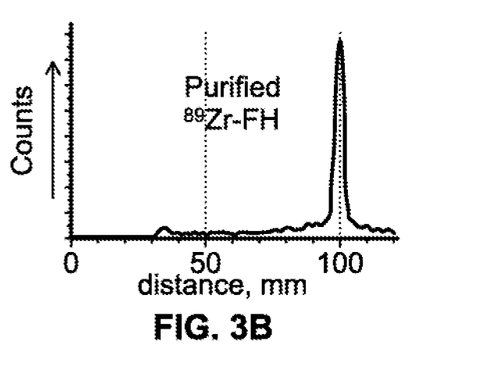
FIG. 3b illustrates TLC of HIR of $^{89}$Zr-FH purified by size exclusion chromatography (SEC).

$^{89}$Zr-FH was purified by size exclusion chromatography (see FIG. 3a), with the purity of $^{89}$Zr-FH fraction confirmed by TLC (see FIG. 3b). TLC indicated the $^{89}$Zr-FH obtained by SEC to be greater than 97% pure. Purity was also evident by SEC rechromatography of the $^{89}$Zr-FH (see, e.g., the 0 hour time point of FIG. 3e).

Figure 3C:
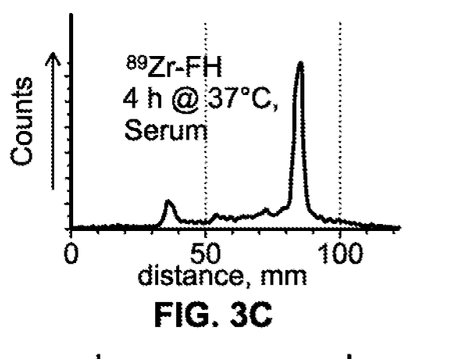
FIG. 3c illustrates the stability of $^{89}$Zr-FH incubated in mouse serum at about 37° C. for about 4 h, as analyzed by TLC.
Figure 3D:
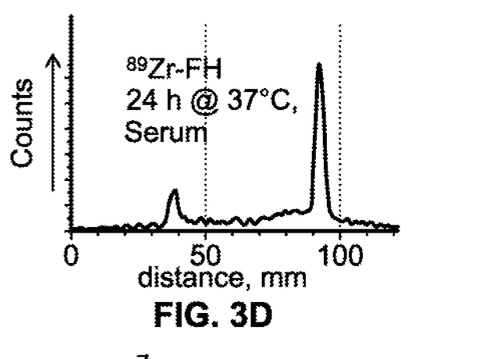
FIG. 3d illustrates the stability of $^{89}$Zr-FH incubated in mouse serum at about 37° C. for about 24 h, as analyzed by TLC.
Figure 3E:
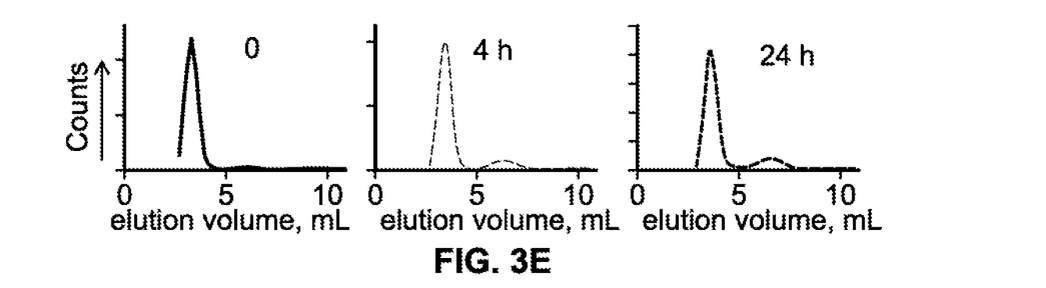
FIG. 3e illustrates SEC chromatograms performed after a DFO challenge consisting of incubating $^{89}$Zr-FH with about 10 mM Tris at a pH of about 7.6 and about 10 µM DFO for up to about 24 hours.
Figure 3F:
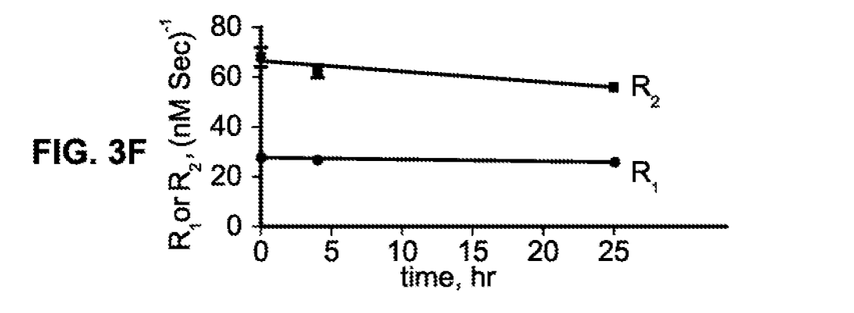
FIG. 3f illustrates the stability of FH in mouse serum by MR relaxometry (values are means±1 s.d., n=3).

Three types of stability studies were performed. First, the stability of $^{89}$Zr-FH was examined in a biological media, mouse serum, by TLC. As shown by FIGS. 3c and 3d, more than 90% of the label was present as $^{89}$Zr-FH even after 24 h. Second, the stability of $^{89}$Zr-FH was examined in presence of the strong iron and zirconium chelator DFO, a procedure termed the "DFO Challenge." As shown by FIG. 3e, when $^{89}$Zr-FH was incubated in about 10 mM Tris at a pH of about 7.6 containing about 10 μM DFO for up to about 24 h and analyzed by SEC, more than 90% of the label was present as $^{89}$Zr-FH. Since the blood half-life of $^{89}$Zr-FH was about 1.02 h, the initial stability time point of about 4 h (FIGS. 3c and 3e) was found to correspond to the clearance of approximately 94% the dose. Third, the stability of non-radiolabeled in FH in mouse serum by relaxometry was examined. This was done to see if FH might dissolve in serum and form high molecular $^{89}$Zr complexes with serum proteins. The dissolution of the FH crystal was generally accompanied by a loss of superparamagnetism and a decrease in R1 and R2 relaxivities, while aggregation yielded an increase in the R2 relaxivity. As shown in FIG. 3f, the R1 and R2 relaxivities were generally constant in mouse serum. Thus, the HIR procedure yielded a generally pure, stable $^{89}$Zr-FH suitable for PET imaging studies. More data may be found at Boros, E. at al., "Chelate-Free Metal Ion Binding and Heat-Induced Radiolabeling of Iron Oxide Nanoparticles," DOI: 10.1039/C4SC02778G, CHEM. SCI. 2015, which is hereby incorporated by reference in its entirety.

In one example, $^{89}$Zr$^4$:FH was synthesized by heating followed by the addition of a quenching agent. About 1M of Na$_2$CO$_3$ was added to about 125 μCi of $^{89}$Zr oxalate (about 380 μL) to bring the pH to about 8.5, which was checked with pH paper. The resulting mixture was then added to a 2 mL conical Reactivial. About 100 μL of chelex-treated water and FH (about 50 μL, including about 1.5 mg Fe) was then added. The vial was sealed, and the mixture was heated with magnetic stirring for about 2 hours at about 120° C. A quenching agent (e.g., desferoxamine (DFO) mesylate), which strongly bound the $^{89}$ZT$^{4+}$ ions to the FH, was then added. The quenching agent was used to stop the formation of $^{89}$Zr$^4$:FH, to dissociate any loosely bound $^{89}$Zr$^{4+}$ from the FH nanoparticle, and to assist in ensuring that any $^{89}$Zr$^{4+}$ that remained was tightly bound to FH.

Figure 4:
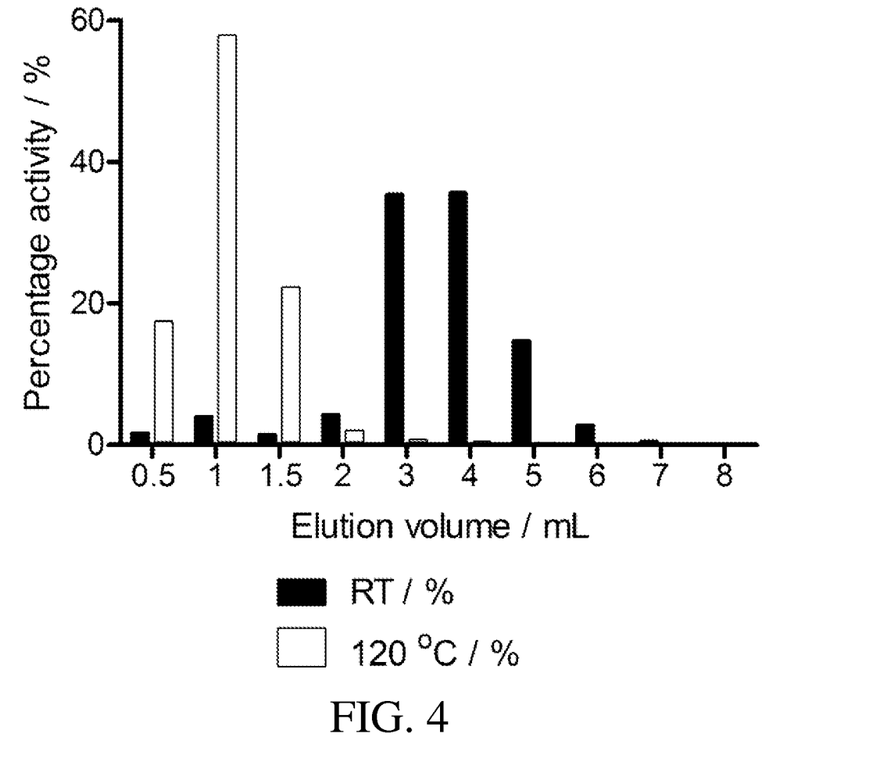
FIG. 4 shows a bar graph illustrating separation of $^{89}$Zr-radiolabeled FH according to one embodiment.
Figure 5:
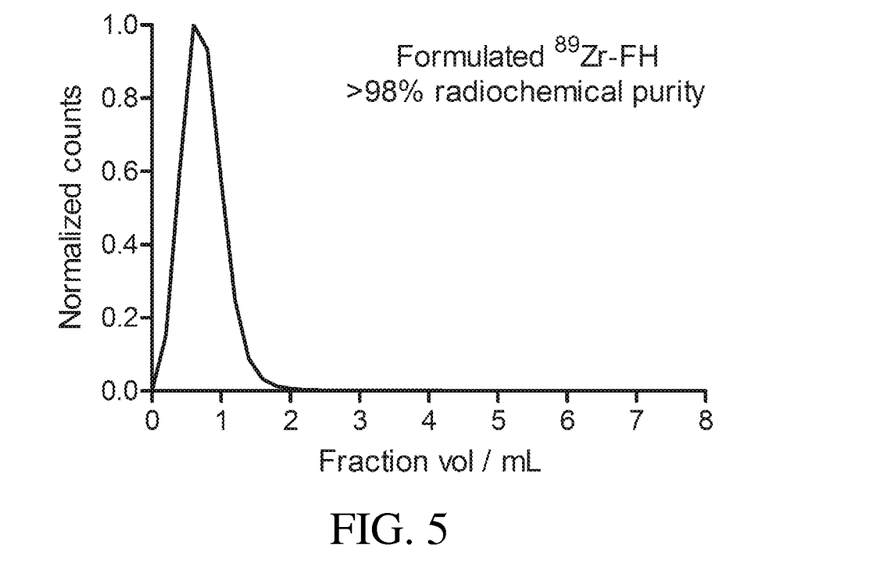
FIG. 5 is a line graph illustrating greater than about 98% radiochemical purity of the sample from FIG. 4.

After the addition of the DFO quenching agent, the association of the FH nanoparticle and $^{89}$Zr$^{4+}$ was indicated by PD-10 gel filtration gel chromatography. It was also indicated by silica gel chromatography using optical and radiographic methods of detection. In these methods, FH appears yellow/orange on thin layer silica gel chromatography and can be easily visualized FIG. 4 illustrates an example of crude separation of radiolabeled $^{89}$Zr-FH after reactions conducted at about 120° C. and about room temperature (RT). The separation was conducted on a PD-10 size-exclusion column eluted with sterile saline. The first bar in each pair of bars of FIG. 1 indicates the percentage activity at about room temperature, and the second bar in each pair indicates the percentage activity at about 120° C. Isolation of radiolabeled high molecular weight (greater than about 30 kDa) material, eluted in the first about 0 mL to about 2.0 mL fractions (the first 3 pairs of bars from the left shown in FIG. 1) was achieved by size-exclusion chromatography on a PD-10 SEPHADEX® G-25 medium column (GE Healthcare, Sweden). The room temperature reaction served as a control indicating that elevated temperatures (greater than about 20° C.) are generally required for $^{89}$Zr labeling of FH. FIG. 2 illustrates the results of an analytical PD-10 size-exclusion analysis confirming that the radiochemical purity of the formulated $^{89}$Zr-FH (in sterile saline) sample was greater than about 98%.

Figure 6:
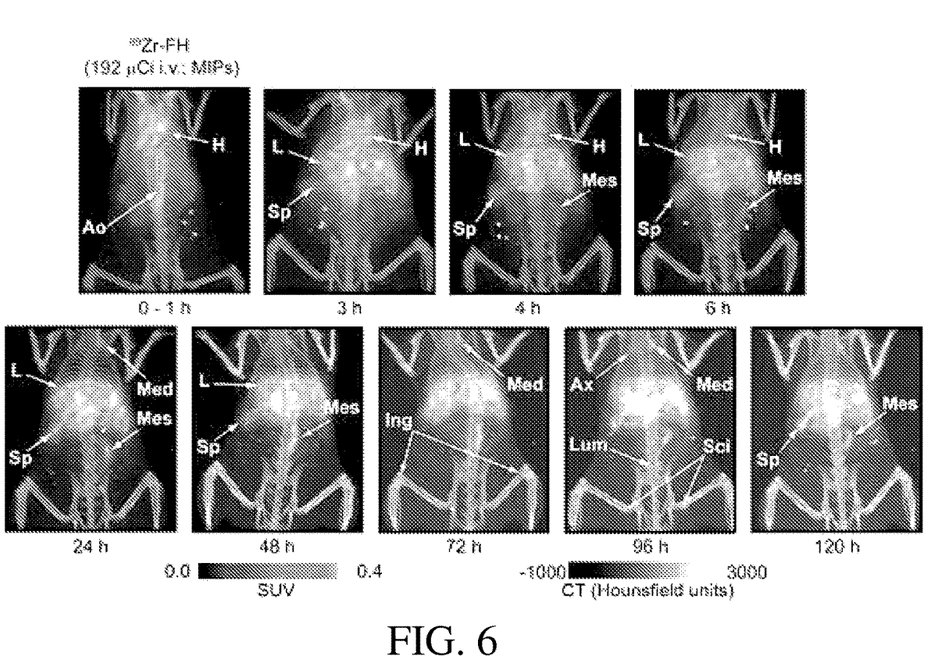
FIG. 6 shows temporal maximum intensity projection (MIP) PET/CT images of a mouse, post-IV, with tail administration of $^{89}$Zr-FH.

The $^{89}$Zr$^{4}$:FH was injected (IV, tail vein) into a C57B6 mouse, and coronal images were taken on a small-animal PET/CT scanner (e.g., a SEDECAL™ PET/CT scanner, available from Sedecal, Spain). The results are shown in the coronal PET images with heat labeled $^{89}$Zr:FH of FIG. 6. Namely, FIG. 6 shows temporal maximum intensity projection (MIP) PET/CT images of a female C57B6, 8-week-old mouse, post-IV, with tail administration of $^{89}$Zr-FH (192 µCi in 200 µL sterile saline). In FIG. 6, H refers to heart, Ao refers to aorta, L refers to liver, Sp refers to spleen, Mes refers to mesenteric lymph node, Med refers to mediastinal lymph nodes, Lum refers to lumbar lymph nodes, Ing refers to inguinal lymph nodes, Ax refers to axial lymph nodes, and Sci refers to sciatic lymph nodes.

As shown in FIG. 6, at about 3 hours post-injection, $^{89}$Zr$^{4}$:FH was in the blood (blood of heart), which is consistent with FH's blood half-life of about 1 hour in mice, and was partially cleared by the liver and spleen. $^{89}$Zr$^{4}$:FH could be seen in mesenteric lymph nodes and in other lymph nodes such as, for example, the mediastinal, axillary, lumbar, sciatic, and inguinal lymph nodes. IV-injected nanoparticles accumulate to high concentrations in the mesenteric lymph nodes or rodents.

As demonstrated in, e.g., the examples discussed above, HIR is a unique labeling concept that exploits several features of FH NP chemistry and the behavior of NPs after injection. First, HIR exploits FH's temperature stability, evident from the use of terminal sterilization step in its manufacture. Second, HIR exploits the pH dependent stability of FH to iron chelators. This enables HIR to employ a DFO stripping reaction, the addition of DFO after the loading step, to pull loosely bound $^{89}$ZT$^{4}$ off the NP without NP dissolution. The stability of superparamagnetic iron oxides to chelators at a generally neutral pH is exploited through the use of citrate as a surface active agent for superparamagnetic iron oxide NPs. Finally, HIR exploits the ability of the macrophage phagocytic clearance mechanisms to clear large amounts of injected NPs. Radiolabeled peptides or antibodies bind to small numbers of receptors and require the injection of low masses of injected tracer with needed radioactivity, e.g., high specific activity tracers. Macrophage-targeted MRI agents (e.g. FERIDEX I.V. (AMAG Pharmaceuticals, Inc., Lexington, Mass.) or COMBIDEX® (AMAG Pharmaceuticals, Inc., Lexington, Mass.), or RESOVIST (Schering Aktiengesellschaft, Germany) and Supravist (Schering Aktiengesellschaft, Germany)) inject between about 20 mg and about 300 mg of Fe per human. Because the body's clearance mechanisms for injected NPs can generally handle large amount of NPs, the HIR loading reaction can be performed under conditions where moles of iron vastly exceed the moles of radiometal, a situation generally not possible where high specific activity tracers (e.g. radiolabeled peptides, radiolabeled antibodies) are required.

The loading reaction of the HIR methods described herein (e.g., about 2 hours at about 120° C. using about 1 mg Fe) led to the binding of $^{64}$Cu, $^{111}$In, and $^{89}$Zr to the FH NP (see FIGS. 2a-2f), a binding that was sufficiently tight to survive the DFO stability challenge (see FIG. 3e, which illustrates stability challenge results for $^{89}$Zr-FH). Thus, the use of heat to induce binding may be applicable to metals other than $^{89}$Zr.

The HIR procedures described herein may be used to label widely available, approved NP drugs without covalent modification, chelate attachment, or the use of organic solvents. The simplicity of the HIR procedures may reduce the barriers to radiolabeled NP imaging research and/or the barriers associated with the clinical use of radiolabeled NP imaging agents.

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

What is claimed is:

1. A method of synthesizing a radiolabeled nanoparticle, the method comprising:
   (i) heating a solution to a predetermined temperature range, the solution including an unlabeled nanoparticle and at least one radioactive metal ion, the unlabeled nanoparticle including an iron oxide and a polymer coating, the at least one radioactive metal ion being configured to directly bind to the iron oxide of the unlabeled nanoparticle to form a radiolabeled nanoparticle,
      wherein the predetermined temperature range is about 80° C. to about 150° C., and
      wherein the unlabeled nanoparticle and the radiolabeled nanoparticle are substantially physically identical except for the resulting radioactivity of the radiolabeled nanoparticle;
   (ii) adding a stripping agent to the solution to complex with non-bound radioactive metal ions remaining in the solution; and
   (iii) separating the complexed stripping agent from the radiolabeled nanoparticle.

2. The method of claim 1, wherein the unlabeled nanoparticle comprises ferumoxytol.

3. The method of claim 1, wherein the at least one radioactive metal ion includes $^{64}$Cu$^{2+}$, $^{89}$Zr$^{3+}$, $^{67}$Ga$^{3+}$, $^{111}$In$^{3+}$, $^{99m}$Tc, $^{99m}$Tc, $^{57}$Co$^{2+}$, $^{177}$Lu$^{3+}$, $^{90}$Y$^{3+}$, $^{223}$Ra$^{2+}$, $^{225}$Ac$^{3+}$, or any combination thereof.

4. The method of claim 1, wherein the solution is a basic solution.

5. A method of removing a radioactive metal ion from solution, the method comprising:
   (i) heating a solution to a predetermined temperature range, the solution including an unlabeled nanoparticle and at least one radioactive metal ion, the unlabeled nanoparticle including an iron oxide and a polymer coating, the at least one radioactive metal ion being configured to directly bind to the iron oxide of the unlabeled nanoparticle to form a radiolabeled nanoparticle, wherein the unlabeled nanoparticle and the radiolabeled nanoparticle are substantially physically identical except for the resulting radioactivity of the radiolabeled nanoparticle;

(ii) adding a stripping agent to the solution to complex with non-bound radioactive metal ions remaining in the solution; and (iii) removing the complexed stripping agent from the solution.

6. The method of claim 1, wherein the stripping agent further complexes with loosely bound radioactive metal ions remaining in the solution.

7. The method of claim 5, wherein the iron oxide nanoparticle is polymer-coated.

8. The method of claim 5, wherein the stripping agent further complexes with loosely bound radioactive metal ions remaining in the solution.

9. The method of claim 5, further comprising cooling the solution containing the complexed stripping agent and the radiolabeled nanoparticle to a temperature of from about 20° C. to about 30° C.

10. The method of claim 6, wherein an association between the at least one radioactive metal ion and the iron oxide is tight.

11. The method of claim 6, wherein the loosely bound radioactive metal ions are loosely bound to the polymer.

12. The method of claim 6, wherein a second radioactive metal ion is configured to loosely bind to the polymer coating of the unlabeled nanoparticle.

13. The method of claim 12, further comprising adding a stripping agent to the solution to complex with the second radioactive metal ion loosely bound to the polymer coating of the unlabeled nanoparticle.

14. The method of claim 5, wherein the predetermined temperature range is about 80° C. to about 150° C.

* * * * *

UNITED STATES PATENT AND TRADEMARK OFFICE
CERTIFICATE OF CORRECTION

| | |
|---|---|
| PATENT NO. | : 10,688,201 B2 |
| APPLICATION NO. | : 15/027927 |
| DATED | : June 23, 2020 |
| INVENTOR(S) | : Holland et al. |

It is certified that error appears in the above-identified patent and that said Letters Patent is hereby corrected as shown below:

In the Specification

At Column 1, Line 13:
Insert the following heading and paragraph:
--GOVERNMENT SUPPORT
This invention was made with government support under EB009691, and EB011996 awarded by the National Institutes of Health. The government has certain rights in the invention.--

Signed and Sealed this
Second Day of May, 2023

Katherine Kelly Vidal
*Director of the United States Patent and Trademark Office*